United States Patent
Koerzdoerfer et al.

(10) Patent No.: US 11,609,295 B2
(45) Date of Patent: Mar. 21, 2023

(54) MAGNETIC RESONANCE IMAGING AND MOTION DETECTION

(71) Applicant: Siemens Healthcare GmbH, Erlangen (DE)

(72) Inventors: Gregor Koerzdoerfer, Erlangen (DE); Mathias Nittka, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 352 days.

(21) Appl. No.: 16/830,445

(22) Filed: Mar. 26, 2020

(65) Prior Publication Data
US 2020/0319284 A1 Oct. 8, 2020

(30) Foreign Application Priority Data
Apr. 3, 2019 (EP) .................................. 19167020

(51) Int. Cl.
*G01R 33/565* (2006.01)
*A61B 5/055* (2006.01)
*G01R 33/483* (2006.01)

(52) U.S. Cl.
CPC ........ *G01R 33/56509* (2013.01); *A61B 5/055* (2013.01); *G01R 33/4835* (2013.01)

(58) Field of Classification Search
CPC ........ G01R 33/48; G01R 33/50; G01R 33/54; G01R 33/543; G01R 33/561; G01R 33/5612; G01R 33/5613; G01R 33/5616; G01R 33/5614; G01R 33/482; G01R 33/4828; G01R 33/483; G01R 33/4835; G01R 33/56509; G01R 33/5673; A61B 5/055
See application file for complete search history.

(56) References Cited

U.S. PATENT DOCUMENTS

| | | | | |
|---|---|---|---|---|
| 2011/0101978 | A1* | 5/2011 | Lake | G01R 33/56509 324/309 |
| 2015/0253409 | A1* | 9/2015 | Feiweier | G01P 21/00 324/322 |
| 2016/0091591 | A1 | 3/2016 | Grodzki | |
| 2018/0014805 | A1* | 1/2018 | Ertel | G01R 33/4812 |
| 2021/0244283 | A1* | 8/2021 | Krueger | G16H 30/20 |

OTHER PUBLICATIONS

Chung, Sohae, et al. "Rapid B1+ mapping using a preconditioning RF pulse with TurboFLASH readout." Magnetic resonance in medicine 64.2 (2010): 439-446.
Cruz, Gastão, et al. "Rigid motion-corrected magnetic resonance fingerprinting." Magnetic resonance in medicine 81.2 (2019): 947-961.
European Search Report for European Application No. 19167020.7-1022 dated Oct. 15, 2019.
(Continued)

*Primary Examiner* — Son T Le
(74) *Attorney, Agent, or Firm* — Lempia Summerfield Katz LLC

(57) ABSTRACT

The disclosure facilitates determining patient motion during a magnetic resonance protocol. According to some examples, the patient motion may be corrected or compensated.

17 Claims, 5 Drawing Sheets

(56) References Cited

OTHER PUBLICATIONS

G. Körzdörfer et al: "Prospective motion correction for 2D slice-selective FISP-MRF in the brain using an in-bore camera system", https://submissions.mirasmart.com/ISMRM2019/ViewSubmission.aspx7sbmID=4639, 2018;. pp. 1-2.

Jiang, Yun, et al. "MR fingerprinting using fast imaging with steady state precession (FISP) with spiral readout." Magnetic resonance in medicine 74.6 (2015): 1621-1631.

Körzdörfer, G., P. Speier, and S. Schröter. "Evaluating the influence of motion on FISP-MRF." Proceedings of the 27th Annual Meeting of ISMRM, Paris. vol. 4085. 2018.

Ma, Dan, et al. "Magnetic resonance fingerprinting." Nature 495. 7440 (2013): 187-192.

Maclaren, Julian, et al. "Prospective motion correction in brain imaging: a review." Magnetic resonance in medicine 69.3 (2013): 621-636.

Mehta, Bhairav Bipin, et al. "Image reconstruction algorithm for motion insensitive MR Fingerprinting (MRF): MORF." Magnetic resonance in medicine 80.6 (2018): 2485-2500.

Pfeuffer, J., et al. "Mitigation of spiral undersampling artifacts in magnetic resonance fingerprinting (MRF) by adapted interleaf reordering." Proceedings of the 25th Annual Meeting of ISMRM, Honolulu. vol. 133. 2017. pp. 1-5.

Yu, Zidan, et al. "Exploring the sensitivity of magnetic resonance fingerprinting to motion." Magnetic resonance imaging 54 (2018): 241-248.

Zaitsev, Maxim, et al. "Magnetic resonance imaging of freely moving objects: prospective real-time motion correction using an external optical motion tracking system." Neuroimage 31.3 (2006): 1038-1050.

\* cited by examiner

| 100 | MRI device | 130 | RF switch | 161 | Processor |
| 101 | Patient | 131 | RF transmitter | 162 | Memory |
| 102 | Table | 132 | RF receiver | 700 | Patient motion |
| 110 | Magnet | 140 | Gradient system | | |
| 111 | Bore | 141 | Gradient coils | | |
| 121 | Coil assembly | 150 | Human machine interface | | |

FIG 7
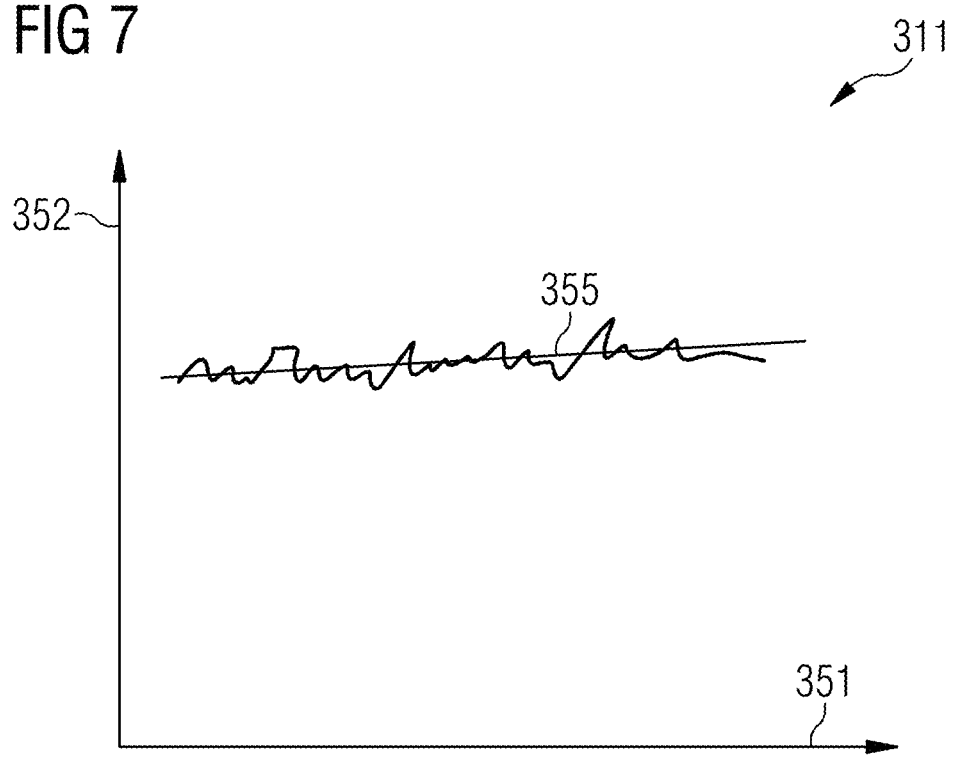
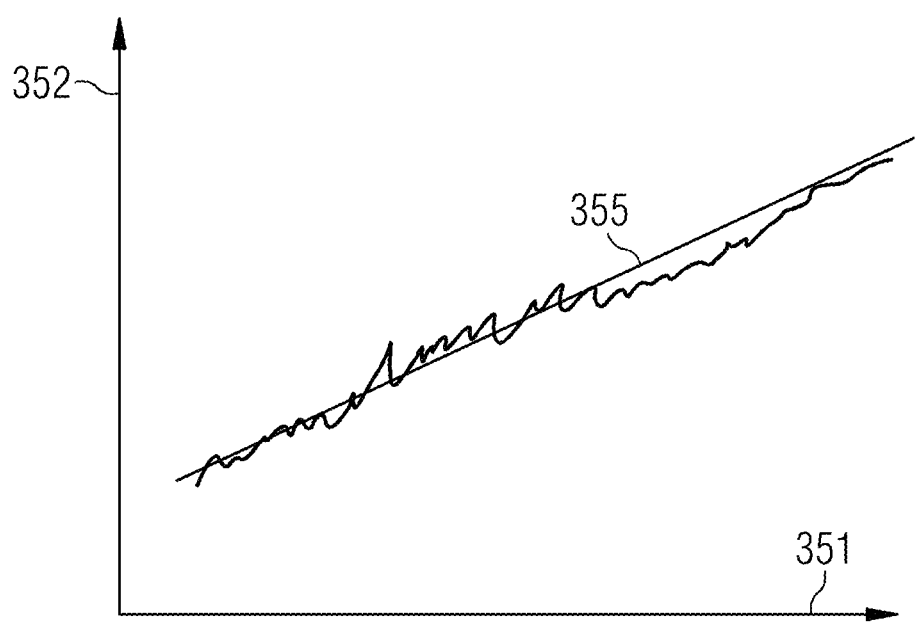

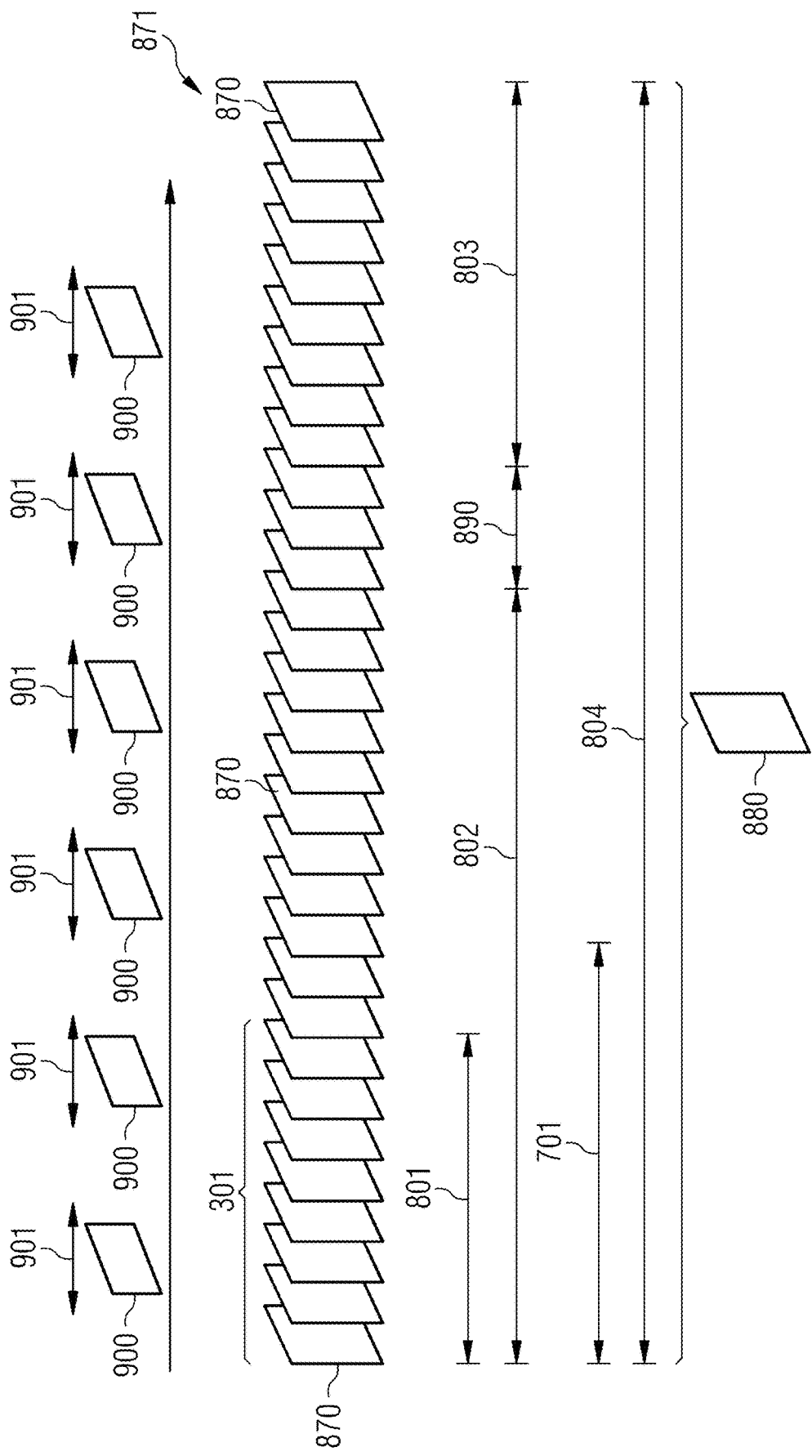

MAGNETIC RESONANCE IMAGING AND MOTION DETECTION

The present patent document claims the benefit of European Patent Application No. 19167020.7, filed Apr. 3, 2019, which is hereby incorporated by reference.

TECHNICAL FIELD

Various examples of the disclosure relate to magnetic resonance imaging (MRI). Various examples specifically relate to using MRI fingerprinting protocols and associated detection of patient motion. Various examples relate to quantitative MRI.

BACKGROUND

Using quantitative MRI, it is possible to determine absolute values of physical observables of the patient. Examples include T1 and T2 relaxation times. In the clinical routine, quantitative MRI is rarely used. Rather, MRI protocols, which are widespread in clinical routine, may rely on a relative contrast for the associated MRI images. For example, different tissue types will appear in the MRI images having a different contrast (sometimes also referred to as weighting). Then, the clinical expert may perform diagnostics based on expert knowledge.

One reason for quantitative MRI not experiencing widespread application in clinical routine is that the associated MRI imaging time, (e.g., the time required to acquire the MRI signals using the MRI protocol), is comparably long. To alleviate this drawback, it has been proposed to use MRI fingerprinting protocols for acquiring the MRI signals. See, e.g. Ma, Dan, et al. "Magnetic resonance fingerprinting." Nature 495.7440 (2013): 187. MRI fingerprinting may rely on a matching of a time evolution of acquired MRI signals with reference MRI signals obtained from a pre-prepared database. This matching may be implemented voxel-by-voxel. The pre-prepared database is sometimes referred to as dictionary. For example, the dictionary may be populated using simulations. For example, the simulations may be subject to different T1 or T2 relaxation times, tissue types, etc. Then, based on the matching, it is possible to quantitatively determine the T1 or T2 relaxation times. For example, the best matching reference MRI signal may be assumed to adequately describe the acquired MRI signals.

It has been observed that patient motion during the acquisition of the MRI signals using the MRI fingerprinting protocol may have an impact on a quality of the MRI images obtained based on the acquired MRI signals. For example, false positives in the matching may result in incorrect qualitative determination of the T1 or T2 relaxation times.

SUMMARY

Therefore, a need exists for advanced techniques of performing MRI, in particular MRI using MRI fingerprinting protocols. More specifically, a need exists for techniques of determining patient motion when performing MRI.

The scope of the present disclosure is defined solely by the appended claims and is not affected to any degree by the statements within this summary. The present embodiments may obviate one or more of the drawbacks or limitations in the related art.

A method of performing MRI includes applying an MRI fingerprinting protocol to acquire MRI signals defining one or more MRI images. The method also includes acquiring a time series of non-MRI images of a body part of a patient, while applying the MRI fingerprinting protocol. Further, the method includes determining a motion of the patient based on object shifts in the time series of non-MRI images.

A computer program or a computer-program product or a computer-readable storage medium includes program code. The program code may be executed by at least one processor. Upon the at least one processor executing the program code, the at least one processor performs a method of performing MRI. This method includes applying an MRI fingerprinting protocol to acquire MRI signals defining one or more MRI images. The method also includes acquiring a time series of non-MRI images of a body part of a patient, while applying the MRI fingerprinting protocol. Further, the method includes determining a motion of the patient based on object shifts in the time series of non-MRI images.

An MRI device is configured to apply an MRI fingerprinting protocol to acquire MRI signals defining one or more MRI images. The MRI device is also configured to acquire a time series of non-MRI images of a body part of a patient, while applying the MRI fingerprinting protocol. Further, the MRI device is configured to determine a motion of the patient based on object shifts in the time series of non-MRI images.

A method of performing MRI includes acquiring MRI signals using an MRI protocol. The method also includes determining an image domain difference map based on a subset of the acquired MRI signals and further based on a reference MRI image of the MRI protocol. The method further includes determining a motion of a patient based on the image domain difference map.

A computer program or a computer-program product or a computer-readable storage medium includes program code. The program code may be executed by at least one processor. Upon the at least one processor executing the program code, the at least one processor performs a method of performing MRI. This method includes acquiring MRI signals using an MRI protocol. The method also includes determining an image domain difference map based on a subset of the acquired MRI signals and further based on a reference MRI image of the MRI protocol. The method further includes determining a motion of a patient based on the image domain difference map.

An MRI device is configured to acquire MRI signals using an MRI protocol. The MRI device is also configured to determine an image domain difference map based on a subset of the acquired MRI signals and further based on a reference MRI image of the MRI protocol. The MRI device is further configured to determine a motion of a patient based on the image domain difference map.

It is to be understood that the features mentioned above and those yet to be explained below may be used not only in the respective combinations indicated, but also in other combinations or in isolation without departing from the scope of the disclosure.

BRIEF DESCRIPTION OF THE DRAWINGS

FIG. 7 schematically illustrates details with respect to the image domain difference map of FIG. 6.

FIG. 8 schematically illustrates acquisition of MRI signals.

DETAILED DESCRIPTION OF EMBODIMENTS

Figure 1:
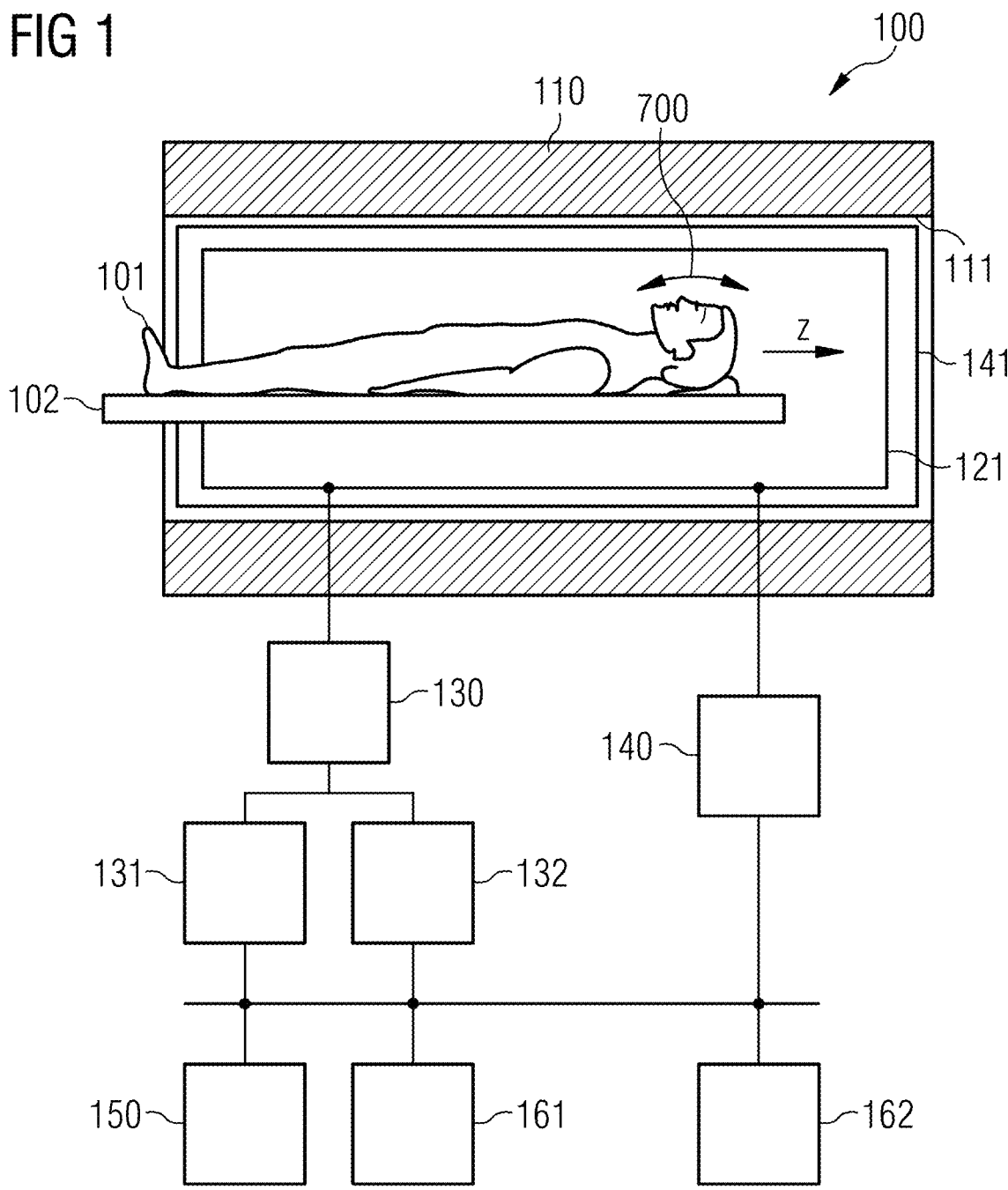
FIG. 1 schematically illustrates an MRI device according to various examples.

Some examples of the present disclosure may provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the disclosure will be described in detail with reference to the accompanying drawings. It is to be understood that the following description of embodiments is not to be taken in a limiting sense. The scope of the disclosure is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Hereinafter, techniques of MRI described. MRI may be employed to obtain raw MRI measurement data of a magnetization of nuclear spins of a sample region of the patient (MRI signals). The sample region defines a field of view. The MRI signals may be defined in k-space. Based on the MRI signals, MRI images in image domain may be determined.

According to various examples, a quantitative MRI protocol may be employed. Hence, the MRI images may have a contrast that allows to determine, in absolute numbers, a physical observable such as T1 relaxation time, T2 relaxation time, tissue type contribution (e.g. water content, fat content), etc. MRI images obtained by applying a quantitative MRI protocol are sometimes referred to as parametric maps.

According to various examples, the MRI signals are acquired by applying an MRI fingerprinting protocol. Here, the k-space of a slice is sampled multiple times. From iteration to iteration, one or more acquisition parameters are re-configured. For example, an orientation of a k-space trajectory along which the k-space is sampled may be re-configured. The iterative sampling yields multiple MRI signals. The MRI signals are iteratively acquired, e.g., one after another/time-multiplexed. The iterative re-configuration of the one or more acquisition parameters helps to obtain a characteristic fingerprint of the response of the nuclear spins of the sample region. Then, it is possible to implement a matching of the acquired MRI signals with reference MRI signals of a dictionary. This allows for reconstruction of an MRI image in image domain. The matching may be implemented voxel-by-voxel. To speed up the acquisition, each iteration may undersample the k-space. This means that, for a given field-of-view or resolution, the number of k-space samples is insufficient to reconstruct the entire image without undersampling artifacts. For example, an echo (e.g., defining a given MR signal) may include a number of samples along a k-space trajectory that is insufficient to reconstruct the MR image at the given FOV and spatial resolution without aliasing.

According to various examples, it is possible to determine motion of the patient (patient motion) during the acquisition of the MRI signals using the MRI fingerprinting protocol. Based on the patient motion, one or more countermeasures may be taken.

Such techniques are based on the finding that, in contrast to the well-known patient motion artifacts in conventional non-quantitative MRI protocols such as visible image distortions, quantitative MRI results may be affected by motion in a subtler way. That is, values in the parametric maps may be corrupted without obvious hints in the appearance of the maps.

This effect may be further emphasized when applying a quantitative fingerprinting MRI protocol. For example, it has been found that two-dimensional (2-D) quantitative fingerprinting MRI protocols are particularly sensitive to through-plane patient motion (as opposed to in-plane patient motion perpendicular to a slice selection direction, e.g., rotation). Examples of through-plane motion may include rigid shifts or tilts. The same also holds for strong 2-D in-plane and three-dimensional (3-D) motion, in case that, e.g., B1+ and B1− affect the signals strong enough.

Hereinafter, techniques are described that facilitate detecting patient motion in particular through-plane patient motion. The techniques described herein do not require MRI-based navigator scans. This makes the techniques simple and fast.

FIG. 1 illustrates aspects with respect to an MRI device 100. The MRI device 100 includes a magnet 110 which defines a bore 111. The magnet 110 may provide a DC magnetic field of one to six Tesla along its longitudinal axis. The DC magnetic field may align the magnetization of the nuclear spins of the patient 101 along the longitudinal axis. The patient 101 may be moved into the bore by a movable table 102.

Illustrated in FIG. 1 is the possibility that patient motion 700 occurs. For example, the patient 101 may nod the head.

The MRI device 100 also includes a gradient system 140 for creating spatially varying magnetic gradient fields (gradients) used for spatially encoding MRI data. The gradient system 140 may include at least three gradient coils 141 that are arranged orthogonal to each other and may be controlled individually. By applying gradient pulses to the gradient coils 141, it is possible to apply gradients along certain directions. The gradients may be used for slice selection (slice-selection gradients), frequency encoding (readout gradients), and phase encoding along one or more phase-encoding directions (phase-encoding gradients). Hereinafter, the slice-selection direction will be defined as being aligned along the Z-axis; the readout direction will be defined as being aligned with the X-axis; and a first phase-encoding direction as being aligned with the Y-axis. A second phase-encoding direction may be aligned with the Z-axis. The directions along which the various gradients are applied are not necessarily in parallel with the axes defined by the coils 141. Rather, it is possible that these directions are defined by a certain k-space trajectory which, in turn, may be defined by certain requirements of the respective MRI sequence and/or based on anatomic properties of the patient 101.

For preparation and/or excitation of the magnetization polarized/aligned with the DC magnetic field, RF pulses may be applied. For this, an RF coil assembly 121 is provided which is capable of applying an RF pulse such as an inversion pulse or an excitation pulse. While the inversion pulse may invert the direction of the longitudinal magnetization, excitation pulses may create transversal magnetization.

For creating such RF pulses, an RF transmitter 131 is connected via an RF switch 130 with the coil assembly 121. Via an RF receiver 132, it is possible to detect signals of the magnetization relaxing back into the relaxation position aligned with the DC magnetic field. In particular, it is possible to detect echoes. Echoes may be formed by applying one or more RF pulses (spin echo) and/or by applying one or more gradients (gradient echo). The magnetization may be inductively coupled with the coil assembly 121 for this purpose. The respectively acquired MRI signals may correspond to raw data in k-space. According to various examples, the MRI measurement data may be post-processed in order to obtain MRI images. Such post-processing may include a Fourier Transform from k-space to image space. Such post-processing may also include reconstruction to avoid aliasing where an undersampling scheme is used. Such reconstruction may employ matching with reference MRI signals obtained from a dictionary.

It may be possible to use separate coil assemblies for applying RF pulses on the one hand side and for acquiring MRI data on the other hand side (not shown in FIG. 1). For example, for applying RF pulses, a comparably large body coil 121 may be used; while for acquiring MRI data, a surface coil assembly including an array of comparably small coils may be used. For example, the surface coil assembly may include 32 individual RF coils and thereby facilitate parallel acquisition techniques (PATs) relying on spatially offset coil sensitivities.

The MRI device 100 further includes a human machine interface 150, e.g. a screen, a keyboard, a mouse, etc. By the human machine interface 150, a user input may be detected and output to the user may be implemented. For example, by the human machine interface 150, it is possible to set certain configuration parameters for the MRI sequences to be applied.

The MRI device 100 further includes a processor 161. The processor 161 may include a GPU and/or a CPU. The processor 161 may implement various control functionality with respect to the operation of the MRI device 100, e.g., based on program code loaded from a memory 162. For example, the processor 161 may implement a sequence control for time-synchronized operation of the gradient system 140, the RF transmitter 131, and the RF receiver 132. The processor 161 may also be configured to implement post-processing for reconstruction of MRI images. For example, matching with reference MRI signals from a dictionary may be employed. The processor 161 may also perform patient motion 700 detection.

Figure 2:
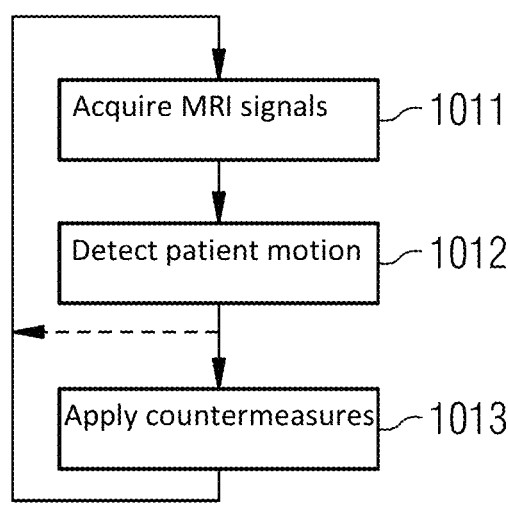
FIG. 2 is a flowchart of a method according to various examples.

Details with respect to the functioning of the processor 161 are described in FIG. 2.

FIG. 2 is a flowchart of a method according to various examples. For example, the method according to FIG. 2 may be executed by the processor 161 of the MRI device 100 according to the example of FIG. 1, e.g., upon loading program code from a memory. It would also be possible that the method is a least partially executed by a separate compute unit, e.g., at a server backend.

In block 1011, MRI signals are acquired. The MRI signals correspond to raw measurement data. The MRI signals may be defined in k-space. The MRI signals define MRI images in image domain. For example, a given MRI signal may correspond to an echo of the nuclear spins. Sampling may be along a k-space trajectory that is defined by gradients.

The MRI signals may be acquired using various MRI protocols. For example, the MRI signals may be acquired using an MRI fingerprinting protocol. The MRI fingerprinting protocol may be defined with respect to (i) acquisition in accordance with one or more acquisition parameters, and (ii) post-processing in accordance with one or more post-processing parameters.

To give a few examples, the one or more acquisition parameters may include: type, shape, amplitude, timing, or repetition rate of RF excitation pulses; type, shape, amplitude, timing, or repetition rate of inversion pulses; type, amplitude, timing, or shape of gradients; readout intervals; k-space trajectory (sometimes also referred to as sampling scheme); undersampling factor (sometimes also referred to acceleration factor); slice selection; 3-D imaging properties; etc.

For example, the one or more acquisition parameters may define a steady-state free-precession (SSFP) with a spiral k-space trajectory, undersampling factor 48, field of view 300 mm, resolution 1.2 mm, and slice thickness 5 mm. See, e.g. Jiang Y. et al, "MR fingerprinting using fast imaging with steady state precession (FISP) with spiral readout," MRM (2015); and Chung S. et al., "Rapid B1+mapping using a preconditioning RF pulse with TurboFLASH readout," MRM (2010); and Pfeuffer, J. et al, "Mitigation of Spiral Undersampling Artifacts in Magnetic Resonance Fingerprinting (MRF) by Adapted Interleaf Reordering," ISMRM (2017).

A few examples of the one or more post-processing parameters include: dictionary content (e.g., reference MRI signals); metric for matching MRI signals and reference MRI signals; etc. For example, the one or more post-processing parameters may facilitate quantitative MRI.

At block 1012, patient motion 700 detection is performed. The patient motion 700 is determined based on measurement data. As a general rule, various options are available for implementing block 1012. Details with regard to these options will be explained in connection with FIG. 4 below.

Based on executing block 1012, it becomes possible to better understand potential impacts of the patient motion 700 on the MRI signals and, hence, on the quality of the associated MRI images. For example, significant patient motion 700 may lead to reduced quality of the associated MRI images. In connection with quantitative MRI, the patient motion 700 may lead to inaccuracies in the determined values of the associated physical observables.

In some examples, it may be desirable to execute block 1013. One or more countermeasures may be performed if patient motion 700 is determined to have taken place. The countermeasures may help to avoid inaccuracies in the interpretation of the content of the MRI images due to artifacts caused by the patient motion 700. The countermeasures may sometimes help to increase the quality of the MRI images in case patient motion 700 is determined to have taken place.

As illustrated in FIG. 2, acquiring of the MRI signals as part of block 1011 need not have to be completed before determining the patient motion 700 in block 1012. In other words, the patient motion 700 may be determined at least partially interleaved with the acquisition of the MRI signals in some of the examples. Thus, online patient motion 700 detection is possible.

Similarly, as illustrated in FIG. 2, in some examples, it would be possible that the one or more countermeasures according to block 1013 are applied even while the acquisition of MRI signals in block 1011 is underway. Then, prospective countermeasures having an impact on the ongoing acquisition of the MRI signals as part of block 1011 would be possible.

Further details regarding one or more countermeasures that may be taken as part of block 1013 are illustrated in connection with FIG. 3. In other words, FIG. 3 illustrates an example implementation of block 1013.

Figure 3:
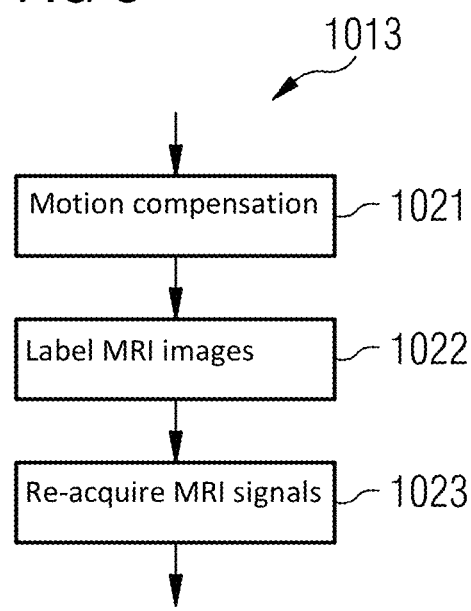
FIG. 3 is a flowchart of a method according to various examples.

FIG. 3 is a flowchart of a method according to various examples. For example, the method according to FIG. 3 may be executed by the processor 161 of the MRI device 100 according to the example of FIG. 1, e.g., upon loading program code from a memory. It would also be possible that the method is a least partially executed by a separate compute unit, e.g., at a server backend.

FIG. 3 illustrates aspects with respect to one or more countermeasures that may be taken in case patient motion 700 is determined to have taken place. In particular, FIG. 3 schematically illustrates various options available regarding countermeasures. As a general rule, it is not required that all of the blocks of FIG. 3 are executed, but rather it would be possible that only one or some of the countermeasures associated with the various blocks in FIG. 3 are executed.

In block 1021, a prospective motion 700 compensation takes place. In block 1021, a re-configuration of one or more acquisition parameters of the MRI fingerprinting protocol is performed, while applying the MRI fingerprinting protocol and, in particular, during the acquisition of the MRI fingerprinting protocol. This is done based on the determined patient motion 700. The re-configuration of the one or more acquisition parameters counteracts the motion 700 of the patient. In other words, the impact of the patient motion 700 is reduced by appropriately adjusting the one or more acquisition parameters of the MRI fingerprinting protocol. To give a few examples, it would be possible to re-configure values of at least one or more of the following acquisition parameters: pulse timing of excitation pulses; excitation slice width; and excitation slice orientation of the MRI fingerprinting protocol.

In further detail, it would be possible to re-configure values defining RF pulses and gradients in such a manner that one and the same region of the patient 101 is sampled, irrespective of the patient motion 700. Thereby, the slice position remains constant relative to the patient (albeit varying along Z-axis defined with respect to the MRI device 100). Thereby, in view of the post-processing of the MRI fingerprinting protocol, it may be provided that the nuclear spins experience the same RF pulses and gradients that have also formed the basis of the simulation used to obtain the associated reference MRI signals of the dictionary. The possibility of nuclear spins that have already been prepared by RF pulses and gradients move out of the slice being sampled and the further possibility of "fresh", unprepared nuclear spins moving into the slice being sampled is thereby mitigated. Such techniques may thus facilitate an auto-tracking of slices in view of patient motion 700.

In block 1022, it is possible that, based on the determined patient motion 700, the MRI images are labelled accordingly. Hence, information tags may be associated with the MRI images. The tags may be indicative of whether the respective MRI images include or not include motion artifacts associated with the patient motion 700. In some examples, it would be possible to label the overall MRI images. In other examples, it would be possible to label one or more regions in the one or more MRI images. Sometimes, it may be possible to identify particular regions in the MRI images that are likely to include the motion artifacts based on the determining of the patient motion 700. For instance, an expert may consider such labels when analyzing the MRI images. To further assist the expert, it would be possible to redact one or more regions that are affected by motion artifacts.

In block 1023, an (at least partial) re-acquisition of MRI signals may be implemented. MRI signals that are impacted by patient motion 700 may thereby be re-acquired, to avoid and impact of the patient motion 700 on the quality of the MRI images.

As a general rule, it would be possible to check whether the motion exceeds a threshold. Then, for strong motion, the acquiring of the MRI signals defining a given slice of multiple slices of the one or more MRI images may be aborted. In block 1023, it would be possible to implement a re-acquisition of the MRI signals that define the given slice. Instead of such re-acquisition, it would also be possible to acquire the MRI signals that define a further slice of the multiple slices different from the given slice.

Aborting acquisition may relate to not finishing the k-space trajectory for a given slice and discarding any acquired samples.

As a general rule, various trigger criteria are conceivable for implementing the re-acquisition of the MRI signals. To give a few examples, it would be possible to monitor for a time lag (e.g., distance in time domain) between (i) determining of the patient motion 700; and (ii) and a possible re-configuration of one or more acquisition parameters in a prospective motion compensation. For instance, it would be possible to determine the time lag between the point in time of executing block 1012 in FIG. 2, and the point in time of executing block 1021 in FIG. 3. This time lag may correspond to a processing delay associated with determining the patient motion 700 and implementing prospective motion correction. For instance, analysis of measurement data associated with the determining of the patient motion 700 may require a certain time, e.g., due to limited computational resources. As a further example, determining how to re-configure one or more acquisition parameters of the MRI fingerprinting protocol based on determined patient motion 700 may also require a certain time. Sometimes, such time lag may be comparably long. In particular, it is possible that this time lag is significantly longer than an exemplary timescale on which the patient motion 700 occurs. This may be detected by performing a comparison between the time lag and the speed of the patient motion 700. Then, it may be decided to re-acquire MRI signals or to not re-acquire MRI signals (e.g., selectively re-acquire), depending on this comparison. For instance, if the time lag is significantly longer than the speed of the patient motion 700, a prospective motion correction may be limited in its effectiveness, because it cannot compensate for a significant fraction of the impact of the patient motion 700. The re-configuration of one or more acquisition parameters of the MRI fingerprinting protocol cannot be applied in a timely manner. In such a scenario, it may be desirable to re-acquire at least some of the MRI signals. Hence, a respective part of the acquisition of the MRI fingerprinting protocol may be re-applied. For example, the RF pulses and gradients defined by the respective acquisition parameters may be again played out.

A further trigger criterion relates to a further comparison between the time lag between the (i) determining of the patient motion 700, and (ii) a repetition rate of pulses or echoes of the MRI fingerprinting protocol. In other words, this time lag is compared with the speed of the acquisition by the MRI fingerprinting protocol. For example, the multiple iterations of the MRI fingerprinting protocol may have a duration that is associated with the repetition rate of pulses or echoes. For example, the time lag to implement prospective motion correction is significantly longer than the speed/progress of the acquisition defined by the MRI fingerprinting protocol, then the prospective motion correction may be limited in its effectiveness, because it cannot compensate for a significant fraction of the impact of the patient motion 700. The re-configuration of one or more acquisition parameters of the MRI fingerprinting protocol cannot be applied in a timely manner. In such a scenario, may be desirable to re-acquire at least some of the MRI signals.

In case at least some of the MRI signals are re-acquired as part of block 1023, then block 1021 may sometimes not need to be executed.

Figure 4:
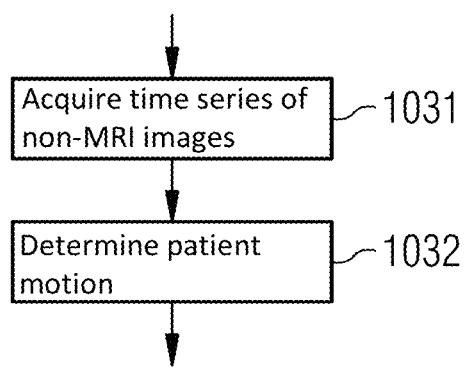
FIG. 4 is a flowchart of a method according to various examples.

FIG. 4 is a flowchart of a method according to various examples. For example, the method according to FIG. 4 may be executed by the processor 161 of the MRI device 100 according to the example of FIG. 1, e.g., upon loading program code from a memory. It would also be possible that the method is a least partially executed by a separate compute unit, e.g., at a server backend. FIG. 4 illustrates aspects with respect to determining patient motion 700.

In the example of FIG. 4, the patient motion 700 is determined based on object shifts in a time series of non-MRI images. The time series of non-MRI images depicts a body part of the patient. The time series of the non-MRI images is acquired in block 1031 while applying the MRI fingerprinting protocol, in particular while acquiring the MRI signals.

By using the non-MRI images, an independent measure of the patient motion 700 is obtained in addition to the MRI signals. Hence, it is not required to interrupt or otherwise delay the acquisition of the MRI signals using the MRI fingerprinting protocol as would be the case, e.g., when using MRI navigator signals.

As a general rule, various imaging modalities may be used to acquire the time series of the non-MRI images. For example, time-of-flight (TOF) imaging may be used or optical imaging using a multi-pixel camera may be used. Ultrasound positioning may be used.

In one example, the time series of non-MRI images includes optical images acquired using an in-bore camera of the MRI device 100.

Then, in block 1032, the patient motion 700 is determined. This is based on object shifts of the depicted body part of the patient between different images of the time series of the non-MRI images. The object shifts describe the time-dependent replacement of the body part. For example, images may be registered pairwise. Object tracking may be implemented. Object detection may be implemented. For example, the head or a certain part of the head (e.g., the eyes) of the patient may be tracked.

Figure 5:
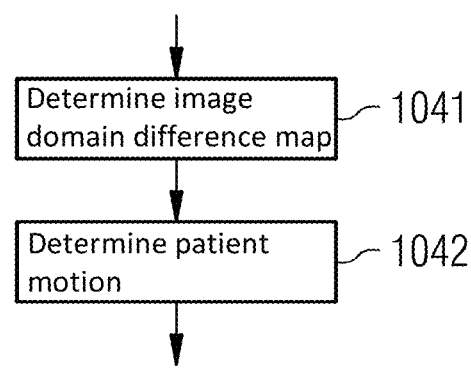
FIG. 5 is a flowchart of a method according to various examples.

FIG. 5 is a flowchart of a method according to various examples. For example, the method according to FIG. 5 may be executed by the processor 161 of the MRI device 100 according to the example of FIG. 1, e.g., upon loading program code from a memory. It would also be possible that the method is a least partially executed by a separate compute unit, e.g., at a server backend. FIG. 5 illustrates aspects with respect to determining patient motion 700.

In the example described by FIG. 5, it is possible to determine the patient motion 700 based on the MRI signals. This means that it is not required to acquire additional measurement data, such as the non-MRI images according to the example of FIG. 4. Notwithstanding the above, in some examples, it may be possible to complement the determining of the patient motion 700 based on the example of FIG. 5 with other techniques.

In the example of FIG. 5, and image domain difference map (e.g., a 2-D image dataset obtained from a comparison) is determined, in block 1041. This image domain difference map is determined based on a subset of the acquired MRI signals (cf. FIG. 2: block 1011); as well as based on a reference MRI image the MRI fingerprinting protocol.

As a general rule, various options are available of obtaining the reference MRI image. For example, the reference MRI image may be obtained from the post-processing of the MRI fingerprinting protocol. In other words, multiple MRI signals acquired using the MRI fingerprinting protocol may be processed to obtain the reference MRI image. More specifically, the count of the multiple MRI signals used to determine the reference MRI image may be larger than the count of the MRI signals of the subset. Further, the reference MRI image may be determined based on MRI signals that are acquired over a certain time duration, the time duration being longer than a time duration of the patient motion 700. In other words, the reference MRI image may include some time domain averaging over the patient motion 700. Thus, an individual event of the patient motion 700 (e.g., the patient turning the head to the left) may not be captured in isolation in the reference MRI image. Rather, there is an averaging over multiple events of the patient motion 700 inherent to the reference MRI image.

As a general rule, it is not required that the reference MRI image is obtained based on all MRI signals of the acquisition of the fingerprinting MRI protocol. Rather, only some of the MRI signals may be used to determine the reference MRI image. This facilitates prospective motion correction, because the reference MRI image is available prior to completion of the acquisition.

Then, at block 1042, the patient motion 700 is determined based on the image domain difference map.

Details with respect to this option for determining the patient motion 700 based on the image domain difference map are explained in connection with FIG. 6.

Figure 6:
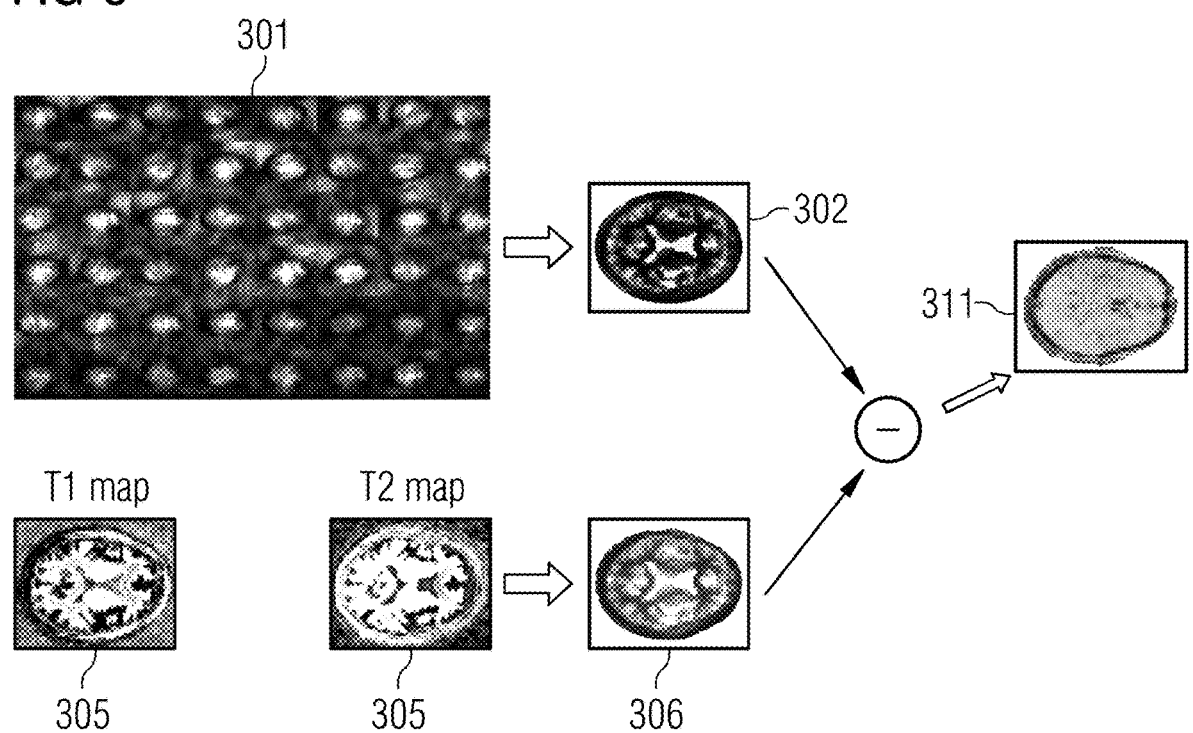
FIG. 6 is a functional flowchart of determining patient motion based on an image domain difference map according to various examples.

FIG. 6 schematically illustrates aspects with respect to determining patient motion 700 based on an image domain difference map 311. FIG. 6 is a corresponding functional flowchart.

In FIG. 6, details with respect to determining the image domain difference map 311 are explained. In the example of FIG. 6, multiple MRI signals of a subset 301 are combined, to thereby obtain an MRI image 302. The MRI signals of the subset 301 have been acquired subsequently in time domain over a certain time duration. The MRI signals may be normalized to yield arbitrary amplitudes. The image domain difference map 311 is then determined based on this MRI image 302. More specifically, the MRI fingerprinting protocol defines an undersampling factor for the acquiring of the MRI signals. In the example of FIG. 6, the undersampling factor is 48. Hence, a total of 48 MRI signals is included in the subset 301 and, thus, combined. As a general rule, the subset 301 may be determined based on the undersampling factor. This process is sometimes referred to as compression. This is done so that the MRI image 302 is essentially fully sampled, e.g., undersampling artifacts are removed or strongly suppressed.

Note that in FIG. 6 the image domain representation of the MRI signals of the subset 301 is combined to yield the MRI image 302.

The time duration over which the MRI signals of the subset 301 are acquired is comparably short, for example, compared to a time duration of the patient motion 700. To give an example, the time duration over which the MRI signals of the subset 301 are acquired may be 1 second or less, optionally not longer than 800 milliseconds. As a general rule, it would be possible to determine the subset 301 (e.g., to assign MRI signals to the subset 301) not only on the undersampling factor, as explained above, but—alternatively or additionally—based on the time duration of the patient motion 700.

This is based on the finding that, thereby, the MRI image 302 may be indicative of an individual event of the patient motion 700 (e.g., the patient 101 turning the head). There may not be a superposition of multiple evens of the patient motion 700 included in the MRI image 302 (different to the reference MRI image 306). Thereby, it becomes possible to accurately determine the patient motion 700.

Various techniques are based on the finding that fingerprinting MRI protocols are particularly suited to such techniques. This is because the fingerprinting MRI protocols implement a fully sampled k-space relatively quickly. This allows to shorten the time duration required to acquire the MRI signals of the subset 301 that essentially fully sample the k-space. This increases the time-resolution of the patient motion detection.

FIG. 6 also illustrates aspects with respect to the reference MRI image 306. Here, to obtain a reference MRI image 306 having a content that is comparable to the content of the MRI image 302, a T1 and T2 weighting is removed from initial MRI reference images 305. These initial MRI reference images 305 may be the native output of the post-processing of the fingerprinting MRI protocol.

Then, next, the MRI image 302 and the reference MRI image 306 are compared, to thereby obtain the image domain difference map 311. The difference map 311, in the scenario FIG. 6, is obtained by subtraction of the MRI image 302 from the reference MRI image 306. Other means for the comparison would be conceivable.

Such comparison may be iteratively re-applied, as the acquisition of the MRI fingerprinting protocol commences. Thereby, time-localized motion 700 may be detected. For instance, as time commences, new subsets 301 may be populated with MRI signals acquired during the respective time durations.

By implementing such a comparison between the MRI image 302 and the reference MRI image 306, the image domain difference map 311 is obtained that includes differences vis-à-vis the reference MRI image 306. These differences may stem from anatomical features (e.g., different tissue) or patient motion 700/motion artifacts. Various techniques are based on the finding that the motion artifacts in the image domain difference map 311 are less localized than the anatomical features (which may be assumed to be statistically distributed). Hence, the motion 700 artifacts are expected to vary on a length scale that is longer than a length scale on which the patient features vary.

FIG. 7 illustrates details with respect to the image domain difference map 311. FIG. 7 illustrates the value 352 of various pixels 351 along a line through the image domain difference map 311, for a scenario without patient motion 700 (top) and for a scenario with patient motion 700 (bottom).

As a general rule, the patient motion 700 may be determined by identifying a baseline of the image domain difference map 311. The baseline may correspond to an image domain low-pass filter. This in particular, in the one the scenario of FIG. 7, this baseline may be approximated by a fit 355 to the pixel values 352.

Various techniques are based on the finding that patient motion 700, in particular, through-plane patient motion 700, experienced in practice may be adequately described by rigid transformations. Such rigid transformations do not include skewing or stretching transformations, but rather define a global shift or rotation.

This finding of rigid through-plane patient motion 700 may be used to accurately define the baseline of the image domain difference map 311, e.g., by imposing certain constraints on the fitting process that yields the fit 355. For example, the baseline may be associated with a 2-D plane. This means that a 2-D plane may be fitted to the image domain difference map 311, to identify the baseline associated with the patient motion 700. This corresponds to a linear fit in 2-D. In the one-dimensional (1-D) representation according to the example of FIG. 7, this would correspond to a linear trendline implementing the fit 355, being characterized by an offset and a slope. Then, the offset and the slope may be indicative of the patient motion 700. Here, a larger magnitude of the offset or slope may correlate with stronger patient motion 700. The sign of the offset or slope may be indicative of the direction of the patient motion 700. The type of the patient motion 700 may correlate with whether offset or slope is observed.

As a general rule, instead of a linear fitting (e.g., 1-D linear fit or 2-D plane fit), it would be possible to use higher order polynomial functions, to account for more complex patient motion 700.

Sometimes, and accuracy achievable by such fitting to identify the baseline of the image domain difference map 311 may be sufficient to accurately determine the patient motion 700. In other examples, such motion artifacts may be superimposed with other artifacts, e.g., flow artifacts resulting from nuclear spins flowing in and/or out of the slice being sampled. In particular, in such scenarios, it may be desirable to apply advanced analytics—going beyond the fitting procedure described above—to determine the patient motion 700 based on the image domain difference map.

For example, the patient motion 700 may in some examples be determined using a machine learning algorithm that obtains the image domain difference map 311 as an input. Such machine learning algorithm may be applied alternatively or additionally to a fitting procedure as explained above. The machine learning algorithm may be used to identify the baseline of the image domain difference map. In other examples, it may not be required to rely on the baseline of the image domain difference map as a characteristic value indicative of the patient motion 700.

The machine learning algorithm may be appropriately trained based on training data that has been annotated using expert knowledge regarding presence/absence of patient motion 700.

Examples of machine learning algorithms include a convolutional neural network or another deep neural network.

Using such an analysis of the image domain difference map using the machine learning algorithm, in some examples, multimodal sensor fusion is possible. For example, the machine learning algorithm may not only obtain the image domain difference map as an input, but it would be rather possible that the machine learning algorithm additionally obtains, e.g., the non-MRI images according to the example of FIG. 4 is a further input.

FIG. 8 illustrates aspects with respect to acquisition of MRI signals 870. FIG. 8 schematically illustrates that a time series 871 of MRI signals 870 is acquired, as part of the MRI fingerprinting protocol. For example, each MRI signal 870 may be associated with a single RF excitation pulse and one or more echoes, e.g., with one or more sampling intervals. For each MRI signal 870, at least a part of the k-space is sampled using a given k-space trajectory.

The overall measurement duration 804 of the MRI fingerprinting protocol is illustrated in FIG. 8. This measurement time duration 804 is used to acquire all MRI signals 870 required to reconstruct an MRI image 880 of a given slice, e.g., at a plane at a given Z-position. The number of MRI signals 870 used to determine the MRI image 880 may be in the order of 100 to 1000, depending on the implementation. From MRI signal 870 to MRI signal 870 one or more acquisition parameters are re-configured, in accordance with a predefined scheme of the MRI fingerprinting protocol. For example, it would be possible that an orientation of a spiral-shaped k-space trajectory is rotated from MRI signal 870 to MRI signal 870.

The process depicted in FIG. 8 is then repeated for multiple slices, at different Z-positions.

FIG. 8 also illustrates aspects with respect to the subset 301 of the MRI signals 870. As illustrated in FIG. 8, only a fraction of all MRI signals 870 acquired during the measurement duration 804 is included in the subset 301. The MRI signals 870 included in the subset 301 are acquired adjacent in time.

As a general rule, it may be desirable to dimension the subset 301 as small as possible, but as large as necessary. This means that the time duration 801 during which MRI signals 870 included in the subset 301 are acquired may be dimensioned as short as possible, but as long as necessary. This finding will be explained in detail next. By dimensioning the time duration 801 as short as possible, it is possible to acquire the MRI signals 870 without averaging across multiple events associated with the patient motion 700. In particular, illustrated in FIG. 8 is an exemplary time duration 701 on which the individual events of the patient motion 700 occur. In this example, the time duration 701 is longer than the time duration 801. At the same time, it may be desirable to acquire sufficient MRI signals 870 during the time duration 801 to essentially fully sample the k-space. This facilitates determining the MRI image 302 (cf. FIG. 6) without undersampling artifacts. It has been found that MRI fingerprinting protocols, (e.g., those using spiral k-space trajectories), offer the surprising and unconventional effect that the time duration 801 may be dimensioned comparably short (e.g., if compared to conventional MRI protocols using Cartesian trajectories): the k-space is sampled quickly. This is achieved in a particularly efficient way for spiral imaging by running the k-space encoding gradients on two (2-D image encoding) or even three (3-D image encoding) independent (orthogonal) axis in parallel. Further on, each spiral trajectory may be configured to cover the center k-space region, which determines the main contrast of the corresponding image. As a general rule, the subset 301 may thus be determined based on the undersampling factor of the MRI fingerprinting protocol, as well as based on the time duration 701 of the patient motion 700.

In FIG. 8, a scenario is illustrated in which the reference MRI image 306 is determined based on the MRI signals 870 acquired during a time duration 802. The time duration 802 is—in the illustrated example—shorter than the overall time duration 804, but significantly longer than, both, the time duration 801, as well as the time duration 701. Thereby, the reference MRI image 306 does not resolve individual events of the patient motion 700 but includes some inherent averaging. This facilitates using the reference MRI image 306 to identify the individual event of the patient motion 700 of the subset 301, by the image domain difference map 311. Within this context, it should be noted that it is most important to detect the fact that motion happened at all, rather than detecting the specific point in time where the motion happened.

Because only a certain fraction of the MRI signals 870 acquired during the time duration 802 is used to determine the reference MRI image 306, it is possible to apply a prospective motion compensation for the MRI signals 870 acquired during the time duration 803. Note that there is also a time lag 890 indicated, required to determine how the one or more acquisition parameters of the MRI fingerprinting protocol are to be reconfigured. As discussed above in connection with FIG. 3, this time lag 890 may be monitored to decide whether or not to re-acquire the MRI signals 870 of the subset 301, or whether a prospective motion correction for the MRI signals 870 acquired during the time duration 803 is sufficient. As a general rule, such a prospective motion correction as illustrated in connection with FIG. 8 is optional. In some examples, it would be possible to perform an off-line motion detection after completing the acquisition and appropriately labelling the MRI image 880 or regions thereof as including motion artifacts. In such a scenario, it would be possible to determine the reference MRI image 306 based on the MRI signals 870 acquired during the entire time duration 804.

As a general rule, to determine the patient motion with some time resolution, it would be possible to determine multiple subsets that are shifted in time domain. For example, a sliding-window process may be used in which adjacent subsets are partially overlapping. The sliding-window process may be used for a prospective motion compensation.

Summarizing, techniques have been described that facilitate to track corrupted MRI images obtained from MRI fingerprinting protocols. The corruption stems from substantial patient motion 700. In particular, through-plane motion 700 (e.g., nodding), which may have a higher effect on the quality of the MRI images than in-plane motion 700 (e.g., shaking head), may be tracked.

In some examples, patient motion 700 may be prospectively corrected by using an in-bore camera system with real-time feedback to re-configure one or more acquisition parameters.

FIG. 8 also illustrates aspects with respect to the optical images 900 that are optionally acquired and that depict, e.g. the head of the patient 101. As illustrated in FIG. 8, a time duration 901 to acquire these optical images 900 may be particularly short. This is because of the optical exposure being fast. Then, assuming that the time lag 890 to determine the motion, e.g. based on an object shift in the optical images 900, and to reconfigure the one or more acquisition parameters is approximately the same for the techniques based on the optical images 900, as for the techniques based on the MRI signals 870 of the subset 301, it follows that the prospective motion correction may be particularly useful when being based on the optical images 900.

Although the disclosure has been shown and described with respect to certain embodiments, equivalents and modifications will occur to others skilled in the art upon the reading and understanding of the specification. The present disclosure includes all such equivalents and modifications and is limited only by the scope of the appended claims. It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

For illustration, various examples have been described with respect to identifying a 2-D plane baseline when determining the motion. In other examples, other types and shapes of baselines may be employed, e.g. second or higher order polynomial functions.

For further illustration, various examples have been described in connection with 2-D MRI protocols. Similar techniques may be applied for 3-D MRI protocols.

For still further illustration, various examples have been described in connection with through plane motion. Similar techniques may be employed for in-plane motion.

For further illustration, various examples have been described in connection with MRI fingerprinting protocols. Similar techniques may be applied to other kinds and types of MRI protocols.

Summarizing, the following examples have been described:

Example 1

A method of performing magnetic resonance imaging, MRI, wherein the method includes: acquiring MRI signals (870) using an MRI protocol; determining an image domain difference map (311) based on a subset (301) of the acquired MRI signals (870) and further based on a reference MRI image (306) of the MRI protocol; and determining a motion of a patient (101) based on the image domain difference map (311).

Example 2

The method of example 1, wherein the motion of the patient (101) is determined by identifying a baseline of the image domain difference map (311).

Example 3

The method of example 2, wherein the baseline is associated with a 2-D plane.

Example 4

The method of any one of the preceding examples, wherein the motion of the patient (101) is determined using a machine learning algorithm obtaining the image domain difference map (311) as an input.

Example 5

The method of any one of the preceding examples, further including combining the MRI signals (870) of the subset (301) to obtain an MRI image (302), wherein the image domain difference map (311) is determined based on the MRI image (302).

Example 6

The method of any one of the preceding examples, further including determining the subset (301) based on an undersampling factor of the MRI protocol.

Example 7

The method of any one of the preceding examples, further including determining the subset (301) based on a time duration (701) of the motion (700).

Example 8

The method of any one of the preceding examples, wherein the reference MRI image is determined based on the MRI signals (870), and wherein the MRI signals (870) are acquired over a time duration that is longer than a time duration of the motion.

Example 9

The method of any one of the preceding examples, wherein the MRI protocol is a fingerprinting MRI protocol.

Example 10

The method of any one of the preceding examples, further including, based on the motion (700) of the patient (101), performing a re-configuration of one or more acquisition parameters of the MRI protocol while applying the MRI protocol.

Example 11

The method of any one of the preceding examples, further including: monitoring a time lag (890) between the determining of the motion (700) of the patient (101) and a re-configuration of one or more acquisition parameters of the MRI protocol based on the motion (700) of the patient (101); performing a comparison between the time lag (890) and a speed of the motion (700); and selectively re-acquiring at least some of the MRI signals (870) depending on the comparison.

Example 12

The method of any one of the preceding examples, further including: monitoring a time lag (890) between the determining of the motion (700) of the patient (101) and a re-configuration of one or more acquisition parameters of the MRI protocol based on the motion (700) of the patient (101); performing a further comparison between the time lag and a repetition rate of pulses or echoes of the MRI protocol; and selectively re-acquiring at least some of the MRI signals (870) depending on the further comparison.

Example 13

The method of any one of the preceding examples, further including, based on the motion (700) of the patient (101), labelling one or more regions in one or more MRI images (880) defined by the MRI signals (870) and which include motion artifacts associated with the motion (700).

Example 14

An MRI device (100) configured to: acquire MRI signals (870) using an MRI protocol; determine an image domain difference map (311) based on a subset (301) of the acquired MRI signals (870) and further based on a reference MRI image (306) of the MRI protocol; and determine a motion of a patient (101) based on the image domain difference map (311).

Example 15

A computer program including program code that may be executed by at least one processor, wherein executing the program code causes the at least one processor to execute the method according to example 1.

The invention claimed is:

1. A method of performing magnetic resonance imaging (MRI), the method comprising:
    applying an MRI fingerprinting protocol to acquire MRI signals defining one or more MRI images;
    acquiring a time series of non-MRI images of a body part of a patient while applying the MRI fingerprinting protocol;
    determining a motion of the patient based on object shifts in the time series of non-MRI images;
    monitoring a time lag between the determining of the motion of the patient and a reconfiguration of one or more acquisition parameters of the MRI fingerprinting protocol based on the motion of the patient;
    performing a comparison between the time lag and a speed of the motion or between the time lag and a repetition rate of pulses or echoes of the MRI fingerprinting protocol; and
    selectively reacquiring at least some of the MRI signals depending on the comparison.

2. The method of claim 1, further comprising:
    performing a reconfiguration of one or more acquisition parameters of the MRI fingerprinting protocol based on the motion of the patient, while applying the MRI fingerprinting protocol.

3. The method of claim 2, wherein the reconfiguration of the one or more acquisition parameters counteracts the motion of the patient.

4. The method of claim 3, wherein the one or more acquisition parameters comprises a pulse timing of excitation pulses of the MRI fingerprinting protocol, an excitation slice width of the MRI fingerprinting protocol, an excitation slice orientation of the MRI fingerprinting protocol, or a combination thereof.

5. The method of claim 2, wherein the one or more acquisition parameters comprises a pulse timing of excitation pulses of the MRI fingerprinting protocol, an excitation slice width of the MRI fingerprinting protocol, an excitation slice orientation of the MRI fingerprinting protocol, or a combination thereof.

6. The method of claim 1, wherein the comparison is between the time lag and the speed of the motion.

7. The method of claim 1, wherein the comparison is between the time lag and the repetition rate of the pulses or the echoes of the MRI fingerprinting protocol.

8. The method of claim 1, further comprising:
    aborting acquiring of the MRI signals defining a given slice of multiple slices of the one or more MRI images when the motion exceeds a threshold; and
    reacquiring the MRI signals that define the given slice or acquiring the MRI signals that define a further slice of the multiple slices different from the given slice.

9. The method of claim 1, further comprising:
    labelling one or more regions in the one or more MRI images that comprise motion artifacts associated with the motion of the patient.

10. The method of claim 1, wherein the time series of non-MRI images comprises optical images acquired using an in-bore camera of an MRI device configured to apply the MRI fingerprinting protocol.

11. The method of claim 1, wherein the motion comprises through-plane motion.

12. A magnetic resonance imaging (MRI) device configured to:
    apply an MRI fingerprinting protocol to acquire MRI signals defining one or more MRI images;
    acquire a time series of non-MRI images of a body part of a patient while applying the MRI fingerprinting protocol;
    determine a motion of the patient based on object shifts in the time series of non-MRI images;
    monitor a time lag between the determining of the motion of the patient and a reconfiguration of one or more acquisition parameters of the MRI fingerprinting protocol based on the motion of the patient;
    perform a comparison between the time lag and a speed of the motion or between the time lag and a repetition rate of pulses or echoes of the MRI fingerprinting protocol; and
    selectively reacquire at least some of the MRI signals depending on the comparison.

13. The MRI device of claim 12, wherein the MRI device is further configured to:
    perform the reconfiguration of the one or more acquisition parameters of the MRI fingerprinting protocol based on the motion of the patient, while applying the MRI fingerprinting protocol.

14. The MRI device of claim 13, wherein the one or more acquisition parameters comprises a pulse timing of excitation pulses of the MRI fingerprinting protocol, an excitation slice width of the MRI fingerprinting protocol, an excitation slice orientation of the MRI fingerprinting protocol, or a combination thereof.

15. The MRI device of claim 12, wherein the comparison is between the time lag and the speed of the motion.

16. The MRI device of claim 12, wherein the comparison is between the time lag and the repetition rate of the pulses or the echoes of the MRI fingerprinting protocol.

17. A non-transitory computer program comprising program code configured to be executed by at least one processor, wherein executing the program code causes the at least one processor to:
- apply a magnetic resonance imaging (MRI) fingerprinting protocol to acquire MRI signals defining one or more MRI images;
- acquire a time series of non-MRI images of a body part of a patient while applying the MRI fingerprinting protocol;
- determine a motion of the patient based on object shifts in the time series of non-MRI images;
- monitor a time lag between the determining of the motion of the patient and a reconfiguration of one or more acquisition parameters of the MRI fingerprinting protocol based on the motion of the patient;
- perform a comparison between the time lag and a speed of the motion or between the time lag and a repetition rate of pulses or echoes of the MRI fingerprinting protocol; and
- selectively reacquire at least some of the MRI signals depending on the comparison.

* * * * *